United States Patent [19]

Wheaton

[11] 4,338,462

[45] Jul. 6, 1982

[54] SILVER-CATALYZED OXIDATION OF METHACROLEIN TO METHACRYLIC ACID

[75] Inventor: Gregory A. Wheaton, Swedesboro, N.J.

[73] Assignee: Atlantic Richfield Company, Los Angeles, Calif.

[21] Appl. No.: 157,623

[22] Filed: Jun. 9, 1980

[51] Int. Cl.³ .................... C07C 51/25; C07C 57/045
[52] U.S. Cl. .................................. 562/533; 562/531; 562/600; 568/881
[58] Field of Search .......................................... 562/533

[56] References Cited

U.S. PATENT DOCUMENTS

| 2,288,566 | 6/1942 | Herstein | 562/533 |
| 2,930,801 | 3/1960 | Montagna et al. | 562/533 |
| 3,387,029 | 6/1968 | Hartel et al. | 562/533 |
| 3,546,286 | 12/1970 | Hartel et al. | 562/533 |
| 3,839,437 | 10/1974 | Wang et al. | 562/533 |

FOREIGN PATENT DOCUMENTS 740005  11/1955  United Kingdom ............... 562/533

*Primary Examiner*—Vivian Garner
*Attorney, Agent, or Firm*—Delbert E. McCaslin

[57] ABSTRACT

In the process for oxidizing methacrolein to a methacrylic acid salt with an oxidizing gas in a strongly alkaline medium at a temperature of 0 to 100° C. and in the presence of a finely divided silver catalyst and recovering methacrylic acid by acidification, the improvement which comprises carrying out said oxidation in the presence of a small amount of dissolved alkali metal carbonate.

7 Claims, No Drawings

SILVER-CATALYZED OXIDATION OF METHACROLEIN TO METHACRYLIC ACID

BACKGROUND OF THE INVENTION

The oxidation of α,β-unsaturated aldehydes to the corresponding α,β-unsaturated carboxylic acids or carboxylic acid salts is well known in the art. Improved yields of the desired acid are known to be obtainable by oxidation of the unsaturated aldehyde with an oxidizing gas in an aqueous alkaline solution in the presence of a silver catalyst. U.S. Pat. Nos. 2,930,801; 3,162,682 and 3,839,437 disclose methacrylic acid production from methacrolein oxidation in a strongly alkaline medium catalyzed with silver as illustrated by the following:

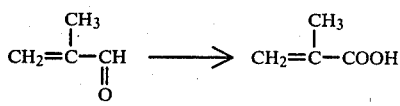

Active life of the silver catalyst is disclosed by U.S. Pat. No. 2,887,496 to be prolonged by conducting such oxidation in the presence of a mixture of triethanolamine and tetrasodium salt of ethylenediaminetetraacetic acid.

Oxidation catalysts having copper (II) oxide alone or in combination with other metals and metal oxides, including silver, are also known. Polyacroleins may be oxidized to corresponding polyacrylic acids as described in U.S. Pat. Nos. 3,387,029 and 3,546,286. Polyacrolein and polymethacrolein oxidation is disclosed to be conducted in an aqueous alkaline solution maintained by an alkali hydroxide or its corresponding carbonate or bicarbonate.

When methacrolein has been oxidized by the prior art alkaline solution silver catalyzed processes, production of the corresponding acid salt is accompanied by the formation of methallyl alcohol and isobutyrate salts as by-products. Formation of those by-products represents a diminution of yield of the desired methacrylate salt and further causes problems in purification of methacrylic acid formed upon acidification of the salt-form product.

SUMMARY OF THE INVENTION

It has been discovered that formation of methallyl alcohol and isobutyrate salt by-products are significantly suppressed by oxidizing methacrolein with an oxidizing gas in a strongly alkaline medium with a silver catalyst in the presence of a small amount of dissolved alkali metal carbonate.

DETAILED DESCRIPTION OF THE INVENTION

Quite unexpectedly, it has been found that the formation of the by-products methallyl alcohol and isobutyrate salts is suppressed during the oxidation of methacrolein with an oxidizing gas in the presence of finely divided silver in an aqueous alkaline medium by the addition of small amounts of alkali metal carbonates to the alkaline medium. By-product methallyl alcohol and isobutyrate salts formed during this improved process are at very low levels, i.e., less than about 0.5 mole percent of methacrolein oxidized. The advantages of this improved process are readily apparent. Higher yields of methacrylate salts are realized and conventional means for purification of the methacrylic acid produced upon acidification of the product mixture is greatly facilitated and simplified.

The alkaline substances and the silver catalysts used in this improved methacrolein oxidation reaction are the same as those described in the prior art, especially the aforementioned U.S. Pat. Nos. 2,930,801; 3,162,682 and 3,839,437. Sodium hydroxide is the preferred alkaline substance but other suitable substances are the hydroxides of potassium lithium, barium, and calcium. The amount of alkaline substance dissolved in water to prepare the aqueous alkaline medium for the oxidation is in excess of the stoichiometric amount of methacrolein to be oxidized. Any concentration of alkaline substance up to about 50% by weight of the aqueous solution may be used. Preferred concentrations are in the range of 15-35% by weight. The aqueous solution of alkaline substance is then saturated with dissolved alkali metal carbonate to produce the aqueous alkaline medium for use in this improved oxidation process. The preferred alkali metal carbonate is sodium carbonate but lithium carbonate and potassium carbonate are also suitable. By virtue of its saturation in the aqueous alkaline medium, the actual concentration of the carbonate additive varies with the concentration of the alkaline substance and the particular alkali metal carbonate employed. In general, however, the carbonate concentration should be less than about 5% by weight of the medium and may be as low as 0.01% by weight. Excessively high carbonate concentrations are to be avoided because deactivation of the silver catalyst can result causing a decreased yield of methacrylate salt.

The oxidizing gas employed is oxygen or oxygen mixed with inert gases. Air is a suitable oxidizing gas.

The operating conditions for this improved oxidation process are similar to those disclosed in U.S. Pat. No. 2,930,801. Oxidation may be carried out at a temperature of from about 0° to 100° C. and the preferred temperature is about 20° to 80° C. The reaction may be conducted at atmospheric pressure or at super atmospheric pressures of oxygen or air. Suitable pressures are from 0 to 200 psig and preferably 0 to 150 psig. The pH of the aqueous reaction mixture should be maintained above about 11.8, and preferably above 12.5, at all times during the oxidation.

Methacrolein oxidation according to this process may also be conducted continuously by simultaneous continuous addition of the aqueous alkaline medium and methacrolein. The alkaline medium is added at a sufficient rate to always maintain a free hydroxide ion concentration of about 1% by weight in the reaction mixture.

On completion of the oxidation of methacrolein, the reaction mixture is filtered to remove the silver catalyst and the filter cake is washed with water. The filtrate and water washings are combined and treated with an acid stronger than methacrylic acid in order to free methacrylic acid from its salt. Suitable acids are mineral acids such as sulfuric acid, hydrochloric acid or nitric acid. Thus obtained methacrylic acid may then be isolated and purified by conventional means.

The following examples serve to further illustrate the present invention which is not limited to the examples.

EXAMPLE I

A twenty percent by weight solution of sodium hydroxide in water was saturated with sodium carbonate by stirring the solution with excess anhydrous sodium carbonate followed by filtration. The resulting solution contained about four percent by weight dissolved sodium carbonate.

A one liter five necked flask equipped with a sintered glass gas diffusion disc in the bottom and a mechanical paddle-type stirrer was charged with 32 grams of silver catalyst, prepared by reducing silver oxide with hydrogen peroxide and sodium hydroxide, and 250 grams of distilled water. The flask was then equipped with a reflex condenser, a thermometer, and an electrode for measuring the pH of the reaction mixture. Stirring was commenced and oxygen gas was introduced into the reaction mixture via the gas diffusion disc at a rate of about 30 liters per hour. The reaction mixture was heated to 50° C. by a water bath and the pH was adjusted to 12.2 using the sodium hydroxide solution which was saturated with sodium carbonate. During a period of about eighty minutes, 34 grams of methacrolein (0.49 mole) was added to the reaction mixture continuously from a syringe using a Sage syringe pump at a rate of 0.50 milliliters per minute. Simultaneously, with the addition of the methacrolein, 89 milliliters of the aqueous sodium hydroxide solution saturated with sodium carbonate were added to the reaction mixture so as to maintain the pH of the reaction mixture above a value of 12.0. The temperature of the reaction mixture was maintained at 50° to 53° C. by means of the water bath.

After completion of the reaction, the reaction mixture was filtered to remove the catalyst. The resulting aqueous solution (495 grams) contained 51.9 grams of sodium methacrylate for a yield of 97 percent based on methacrolein and 0.03 grams of sodium isobutyrate (0.04 percent yield based on methacrolein). The product mixture was acidified with a slight excess of sulfuric acid and was then extracted with diethyl ether. The extract was fractionally distilled in the presence of hydroquinone to give 38.4 grams of methacrylic acid (0.45 mole) for a yield of 92 percent based on methacrolein.

EXAMPLE II

The apparatus described in Example I was charged with 27 grams of silver catalyst and 200 grams of distilled water. Stirring was commenced, and oxygen gas was introduced into the catalyst suspension at a rate of about 30 liters per hour. The pH of the reaction mixture was adjusted to 12.5 using a twenty percent by weight solution of sodium hydroxide which had been saturated with sodium carbonate. During a period of about sixty minutes 24 grams of methacrolein (0.34 mole) was added to the reaction mixture continuously from a syringe using a Sage syringe pump at a rate of 0.48 milliliters per minute. Simultaneously with the addition of the methacrolein, 62 milliliters of the twenty weight percent aqueous sodium hydroxide solution saturated with sodium carbonate were added to the reaction so as to maintain the pH of the reaction mixture above a value of 12.0. The temperature of the reaction mixture was maintained between 28° and 35° C. by means of the water bath. Filtration of the reaction mixture to remove the catalyst gave 320 grams of an aqueous solution containing 34.6 grams of sodium methacrylate (94% yield based on methacrolein), 0.13 gram sodium isobutyrate (0.3% yield based on methacrolein), and 0.06 gram methallyl alcohol (0.2% yield based on methacrolein).

What is claimed is:

1. In the process for oxidizing methacrolein to a methacrylic acid salt with oxygen or oxygen mixed with an inert gas in a strongly alkaline medium at a temperature of 0° to 100° C. and in the presence of a finely divided silver catalyst and recovering methacrylic acid by acidification, the improvement which comprises carrying out said oxidation at a pH of greater than 12.5 in the presence of from 0.01 to 5 percent by weight of dissolved alkali metal carbonate based on the alkaline medium which has a hydroxide concentration of not more than 50 percent by weight.

2. The process according to claim 1 wherein the oxidation temperature is about 20° to 80° C.

3. The process according to claim 2 wherein the alkaline medium is an aqueous solution of sodium hydroxide and sodium carbonate.

4. The process according to claim 3 wherein the alkaline medium contains 15–35% by weight of an alkali metal hydroxide.

5. The process according to claim 1 wherein the strongly alkaline medium comprises an aqueous solution of
    (a) at least one hydroxide selected from the group consisting of sodium hydroxide, potassium hydroxide, lithium hydroxide, barium hydroxide and calcium hydroxide, and
    (b) at least one carbonate selected from the group consisting of sodium carbonate, potassium carbonate and lithium carbonate.

6. The process according to claim 1 wherein the alkaline medium is an aqueous solution saturated with dissolved alkali metal carbonate and contains a hydroxide selected from the group consisting of sodium hydroxide, potassium hydroxide, lithium hydroxide, barium hydroxide and calcium hydroxide in an amount slighly in excess of the stoichiometric amount of methacrolein to be oxidized.

7. The process according to claim 1 wherein methacrolein and the strongly alkaline medium are continuously added to the reaction mixture at respective rates sufficient to maintain a free hydroxide ion concentration of about 1% by weight of the reaction mixture.

* * * * *